US011730514B2

(12) United States Patent
Li et al.

(10) Patent No.: US 11,730,514 B2
(45) Date of Patent: Aug. 22, 2023

(54) REMOVABLE DUAL GOLD MARKER IMPLANTATION DEVICE WITH MINOR DAMAGE AND USING METHOD THEREOF

(71) Applicant: Fujian Medical University Union Hospital, Fujian (CN)

(72) Inventors: Xiaobo Li, Fujian (CN); Benhua Xu, Fujian (CN); Fangfen Dong, Fujian (CN); Fen Zheng, Fujian (CN); Lanyan Guo, Fujian (CN); Jing Chen, Fujian (CN); Liuqing Jiang, Fujian (CN); Qingliang Lin, Fujian (CN); Yimin Wu, Fujian (CN); Miaoyun Huang, Fujian (CN); Daxin Huang, Fujian (CN)

(73) Assignee: Fujian Medical University Union Hospital, Fujian (CN)

( * ) Notice: Subject to any disclaimer, the term of this patent is extended or adjusted under 35 U.S.C. 154(b) by 351 days.

(21) Appl. No.: 17/134,509

(22) Filed: Dec. 28, 2020

(65) Prior Publication Data
US 2022/0015799 A1     Jan. 20, 2022

(30) Foreign Application Priority Data

Jul. 14, 2020  (CN) .......................... 202010674326.8

(51) Int. Cl.
*A61B 17/34* (2006.01)
*A61B 90/00* (2016.01)

(52) U.S. Cl.
CPC ...... *A61B 17/3468* (2013.01); *A61B 17/3403* (2013.01); *A61B 90/39* (2016.02);
(Continued)

(58) Field of Classification Search
CPC ............ A61B 90/39; A61B 2090/3987; A61B 2090/392; A61B 2090/3927; A61B 2090/3954; A61B 2090/3991; A61B 2090/3983; A61B 2090/3966; A61B 2090/3925; A61B 2090/3933; A61B 2090/3937; A61B 2090/3962; A61B 2090/397; A61B 2090/3995;
(Continued)

(56) References Cited

U.S. PATENT DOCUMENTS

| 2008/0033286 A1* | 2/2008 | Whitmore .............. A61B 90/39 600/426 |
| 2019/0167379 A1* | 6/2019 | Näslund ................. A61B 90/39 |

FOREIGN PATENT DOCUMENTS

| CN | 106334273 | 1/2017 |
| CN | 104840256 | 5/2017 |
| CN | 111529966 | 8/2020 |

* cited by examiner

*Primary Examiner* — Majid Jamialahmadi
(74) *Attorney, Agent, or Firm* — JCIP Global Inc.

(57) ABSTRACT

A removable dual gold marker implantation device with minor damage comprises a gold marker and a puncture needle, the gold marker is arranged in the needle barrel of the puncture needle when in use; the gold marker comprises a gold marker head and a connecting wire connected with the gold marker head; the gold marker head comprises a first gold marker, a connecting part and a second gold marker connected in sequence. The disclosure reduces the damage to the body when removing the gold marker, and the dual gold marker structure makes the implantation of multiple gold markers at the same time possible and reduces the number of times of implantation and improves the efficiency.

8 Claims, 4 Drawing Sheets

(52) U.S. Cl.
CPC ............... *A61B 2017/3405* (2013.01); *A61B 2090/3987* (2016.02)

(58) Field of Classification Search
CPC ........ A61B 2090/3904; A61B 17/3468; A61B 17/3403; A61B 17/3405
See application file for complete search history.

REMOVABLE DUAL GOLD MARKER IMPLANTATION DEVICE WITH MINOR DAMAGE AND USING METHOD THEREOF

CROSS-REFERENCE TO RELATED APPLICATION

This application claims the priority benefits of China application serial no. 202010674326.8, filed on Jul. 14, 2020. The entirety of the above-mentioned patent application is hereby incorporated by reference herein and made a part of this specification.

BACKGROUND OF THE DISCLOSURE

1. Field of the Disclosure

The disclosure relates to the technical field of medical devices, in particular to a removable dual gold marker implantation device with minor damage.

2. Description of Related Art

Cyberknife, also known as "stereotactic radiosurgery platform", is the latest whole-body stereotactic radiosurgery equipment in the world. The equipment can treat tumors in all parts of the body, and tumor tissues can be killed with only 3~5 sessions of radiation. It is the only form of whole body radiation surgery with the advantages of "no wound, no pain, no bleeding, no anesthesia, short recovery period", etc. Patients can go home right after surgery.

Along with the development of radiotherapy technology, the development of precision radiotherapy technology improves the curative effect of radiotherapy and reduces side effects. Before Cyberknife treatment, image guidance is often required for implanting the gold marker near the tumor (that is, target area), so as to track the location of the tumor during the Cyberknife treatment, thus achieving accurate treatment. The gold marker usually adopts pure gold particles with a length of 3-5 mm and a diameter of 0.70-0.80 mm. The real-time location of tumor is acquired by digital image, and the therapeutic rays are guided for automatic correction. There are different modes for radiotherapy tracing and image registration, but for the breathing tracking and gold marker tracking of specific radiotherapy equipment (such as the Cyberknife), implantation of gold marker in the body is required, and the existing gold marker is designed on the shape of a cylinder, one is an integrally-smooth cylinder, without structure design, when implanted in the human body the gold marker of such form is easy to lose or displace due to the patient's breathing and cough, it is prone to cause great position deviation in the entire treatment process, resulting in deviation of the cancer treatment and thus affecting the treatment effect.

The patent No. CN201610532532.9 has disclosed a metal marker with a concave structure on the outer surface, and the metal marker is a cylindrical body with a spiral groove on the outer surface. The gold marker with a groove structure can increase the adhesion force of the gold marker to the human body and reduce the risk of the displacement of the gold marker to a certain extent, thus improving the accuracy of the positioning. However since the gold marker itself is small in size, the adhesion force of the gold marker depends on the support and contact provided by the surrounding tissues, the gold marker of such structure can achieve good results when being used in the position such as the internal organs where the tissue structure is compact, but the effect will be greatly reduced when being used in the position such as the lung or bronchus where there are gaps between the tissue structure, and the displacement of the gold marker caused by the patient's breathing and coughing is also obvious.

Another gold marker structure disclosed in CN201510220080.6 comprises: a marker body; and a first anchoring structure comprising: a fixed section, wherein the end of the fixed section is embedded in the marker body, so as to realize the tight connection between the fixed section and the marker body, and prevent relative sliding or displacement between the fixed section and the marker body; a first extending section is arranged at the first end of the fixed section and extends away from the fixed section, and a first spiral section, the starting end of the first spiral section is arranged at the first end of the first extension section, and the terminating end of the first spiral section is located in the extending direction of the first extension section and is spaced apart from the first end of the first extension section. Because of the elastic structure of the spiral, while being implanted to the body, the elastic structure of the end portion can be fixed effectively, thus preventing the displacement of the gold marker.

However, the gold markers in the above three structures are one-time use, and cannot be taken out after being implanted in the body. Since implanting 2-5 gold markers is required each time for realizing the positioning, once the positioning is failed, re-implanting 2-5 gold markers for re-positioning is required, thus resulting multiple gold markers leaving in the patient's body, which will not only increase the cost but also have a certain impact on the patient.

The whole therapeutic process of existing radiotherapy is as follows:

1. Patients see a doctor at the radiotherapy department. When it is confirmed that gold marker implantation radiotherapy is necessary, an appointment for gold marker implantation and an appointment for moulding (i. e., mould for body position fixation during the radiotherapy) one week after gold marker implantation are required.

2. Moulding and positioning, that is, fix the patient by the mould and scan the patient through CT, then transmit the scanned image to the radiotherapy doctor's workstation, which takes a day.

3. The doctor sketches the focus area (target area) according to the patient's condition and the scanned positioning image, which takes 1-3 working days depending on the patient's condition.

4. Medical dosimetrist and physiotherapists work together to make a radiotherapy plan for the patient's focus area, so that the target area matches with the prescribed therapeutic dose and the therapeutic dose received by the surrounding organ is minimized, which needs 1 to 5 days depending on the patient's condition.

5. The patient is treated with radiotherapy until the end of the course of treatment.

Due to the displacement of the gold marker, the treatment can only begin after the completion of the three stages of re-positioning, re-sketching and re-planning, which needs at least 3 to 5 days or even more time, and the time difference for re-positioning caused by incorrect positioning has a big influence on the patient radiotherapy curative effect.

The patent application No. CN202010412486.5 has disclosed a method for the use of a removable gold marker implantation device for human radiotherapy positioning, which includes the following steps:

1. Push the needle core to the bottom, so that the top of the needle core slightly beyond the top of the needle barrel;

2. The puncture needle was implanted into the target area after passing through the body surface;

3. Slowly draw out the needle core to make the channel in the needle barrel empty;

4. Push the gold marker head into the gold marker filling hole, and the gold marker head enters the needle barrel via the funnel-shaped cavity;

5. Slowly push the needle core again to the bottom; the needle core drives the head of the gold marker to the top of the needle barrel;

6. Slowly pull the needle core out of the needle barrel, and then pull out the puncture needle;

7. The rear end of the gold marker reserved on the outside of the body surface shall be fixed on the body surface with medical adhesive tape;

8. Implant the remaining gold markers by repeating step one to step seven, and completing the implantation and fixation of multiple gold markers;

After the whole treatment, tear off the medical adhesive tape that sticks to the body surface, and remove the gold marker head from the body by pulling the rear end of the gold marker.

The removable gold marker can be removed from the body by pulling the rear end of the gold marker, but since it takes almost two-weeks from the implantation of gold markers to the removal of gold markers, the channel left by the puncture needle while implanting the gold marker will gradually heal, and the patient will have obvious pain while removing the gold marker, and the implantation method is the same as the prior art in that only one gold marker can be implanted each time, which is not efficient.

SUMMARY OF THE DISCLOSURE

The present disclosure aims at overcoming the shortcomings of the prior art and provides a removable dual gold marker implantation device which is easy to implant, not easy to shift, convenient to remove and has minor damage.

The disclosure is realized by the following means: a removable dual gold marker implantation device with minor damage comprises a gold marker and a puncture needle; the gold marker is arranged in a needle barrel of the puncture needle when in use; the gold marker comprises a gold marker head and a connecting wire connected to the gold marker head; and the connecting wire is a flexible medical fine line, the gold marker head comprises a first gold marker, a connecting part and a second gold marker connected in sequence; the puncture needle comprises a needle barrel and a needle core; a needle tip is formed at a front end of the needle core and the front end of the needle core is slightly smaller than an inner diameter of the needle barrel; a rear end of the needle barrel is connected with a handle; and an implant chamber is sleeved on the rear end of the needle barrel an interior of the implant chamber is communicated with that of the needle barrel; a guide sleeve is sleeved on the needle barrel; and a rear end of the guide sleeve is slidably connected with a fixed disk.

Further, the first gold marker and the second gold marker are of the same diameter and length.

Further, the length of the connecting part is equal to or greater than 2 cm and less than or equal to 6 cm.

Further, the connecting part is made of a flexible but incompressible material.

Further, a guide hole communicated with the needle barrel is provided in the handle; the top of the guide hole is provided with a position-limiting plate; and the rear end of the needle core is provided with a push-pull part.

Further, the implant chamber comprises an implant chamber cover flexibly connected; a gold marker filling hole communicated with the interior of the needle barrel and a rotating shaft are arranged below the implant chamber cover; a winding sleeve is movably sleeved on the rotating shaft; the connecting wire is enwound on the winding sleeve.

Further, the aperture of the gold marker filling hole is larger than the diameter of the gold marker head and smaller than the length of the gold marker head.

Further, a plurality of wire clamping grooves uniformly spaced apart are circumferentially distributed on the fixed plate;

Further, a foldable flexible folding sheet and a catch groove extend from the upper surface of the fixed plate; the folding sheet is positioned directly above the guide sleeve when being folded; the width of the folding sheet is slightly wider than the diameter of the guide sleeve.

The disclosure relates to a method of use of a removable dual gold marker implantation device with minor damage, which comprises the following steps:

1. Put the gold marker into the needle barrel through the implant chamber;

2. Implant the puncture needle into the target area after passing through the body surface;

3. Push the needle core to the bottom; the needle tip pushes the gold marker out of the needle barrel to the target area;

4. Hold the handle and remain stationary, slide the fixed plate, so that the fixed plate is attached to the patient's skin where the puncture needle is pierced through;

5. Press the fixed plate tightly and hold the guide sleeve to slowly draw the needle barrel out from the guide sleeve;

6. Clamp the guide sleeve and the connecting wire in the guide sleeve into one of the clamping grooves after the needle barrel is drawn out;

7. Press the folding sheet so that a head portion of the folding sheet is in clamping fit with the catch groove and the guide sleeve thus is being compressed tightly by the folding sheet;

8. After the whole treatment, unfold the folding sheet, remove the guide sleeve from the wire clamping groove and pull the connecting wire so that the gold marker head is separated from the body smoothly along the guide sleeve;

9. Hold the fixed plate and the guide sleeve simultaneously and slowly pull the guide sleeve outward, thus removing the guide sleeve from human body.

The beneficial effect of the disclosure is that the implantation method by the cooperation between the puncture needle and the guide sleeve provides a more convenient way for removing the gold marker, and reduces the harm to the body when removing the gold marker. Further, the guide sleeve provides more stable support for the gold marker in the body, thus effectively preventing the positioning failure caused by the displacement of the gold marker. The dual gold marker structure makes the implantation of multiple gold markers at the same time possible, which reduces the number of times of implantation and improves the efficiency.

BRIEF DESCRIPTION OF THE DRAWINGS

In order to give a clearer description of the technical scheme of the embodiments of the disclosure, a brief description of the accompanying drawings to be used in the embodiments is given below. It should be understood that the following accompanying drawings show only some embodiments of the present disclosure, and therefore should not be regarded as limiting the scope. For those skilled in the art, other relevant accompanying drawings can be obtained on the basis of these accompanying drawings without the cost of creative labor.

DESCRIPTION OF THE EMBODIMENTS

In order to explain the purpose, technical scheme and advantages of the embodiments of the disclosure more clear, the technical scheme of the embodiments of the disclosure will be clearly and completely described according to the accompanying drawings, and it is obvious that the embodiments of the disclosure are a part of the embodiments of the disclosure. Based on the embodiments of the disclosure, all other embodiments obtained by those skilled in the art without creative labor are within the scope of protection of the disclosure. Therefore, the descriptions of the above specification and embodiments are intended to explain the protection scope of the present disclosure, but do not constitute a limitation to the protection scope of the present disclosure. Based on the embodiments of the disclosure, all other embodiments obtained by those skilled in the art without creative labor are within the scope of protection of the disclosure.

In the description of the disclosure, the terms "up", "down", "interior", "outside", "front end", "rear end", "both ends", "one end", "the other end" and the like are the orientations and position relationships shown based on the drawings, and the orientations and position relationships are for ease of description only and do not imply that the apparatus or element referred to must have a specific orientation or be constructed and operated in a specific orientation; therefore, these terms cannot be interpreted as a limitation to the specific protection scope of the present disclosure. Moreover, the terms "first" and "second" are used only for descriptive purposes and cannot be interpreted as indicating or implying relative importance.

In the description of the disclosure, it is necessary to state that, unless otherwise expressly specified and defined, the terms "installation", "comprising", "connection", etc. shall be understood in a broad sense, such as "connection" could be fixed connection, a detachable connection, or an integrated connection; either a mechanical connection, or an electrical connection; a direct connection, or an indirect connection through an intermediate medium, or an internal connection between two elements. For those skilled in the art, the specific meaning of the term in the disclosure should be understood according to specific situation.

Embodiment I

Figure 1:
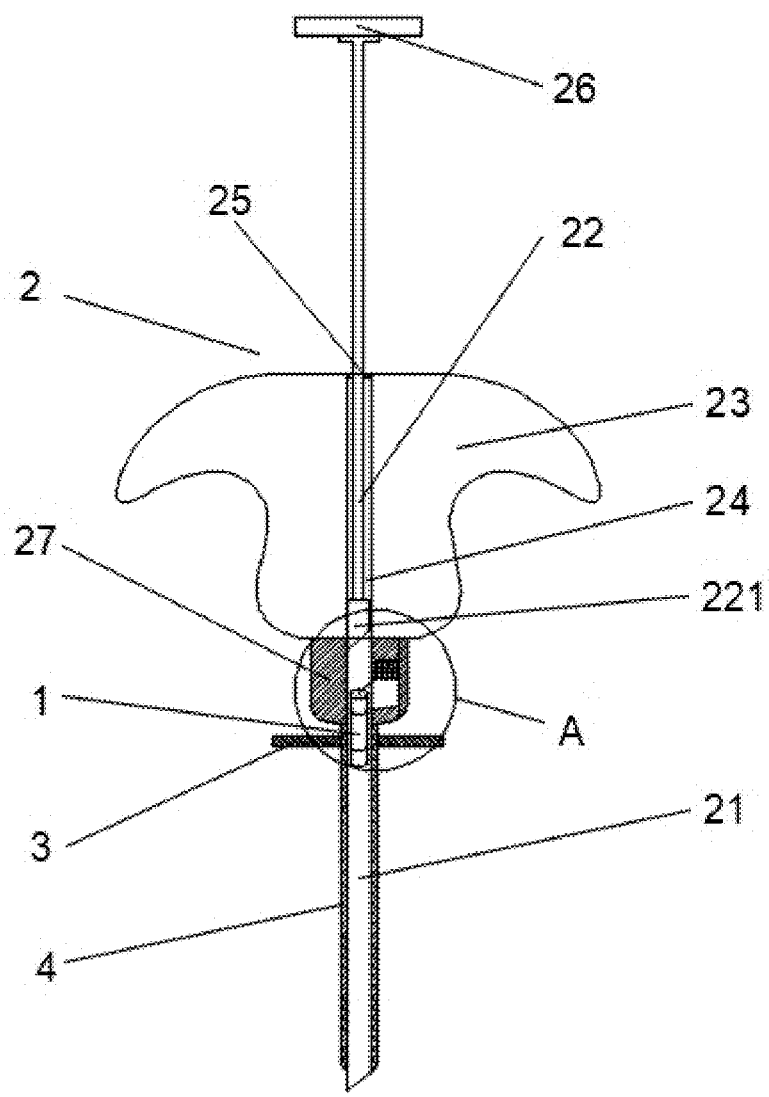
FIG. 1 is a structural schematic of the embodiments of the disclosure.
Figure 2:
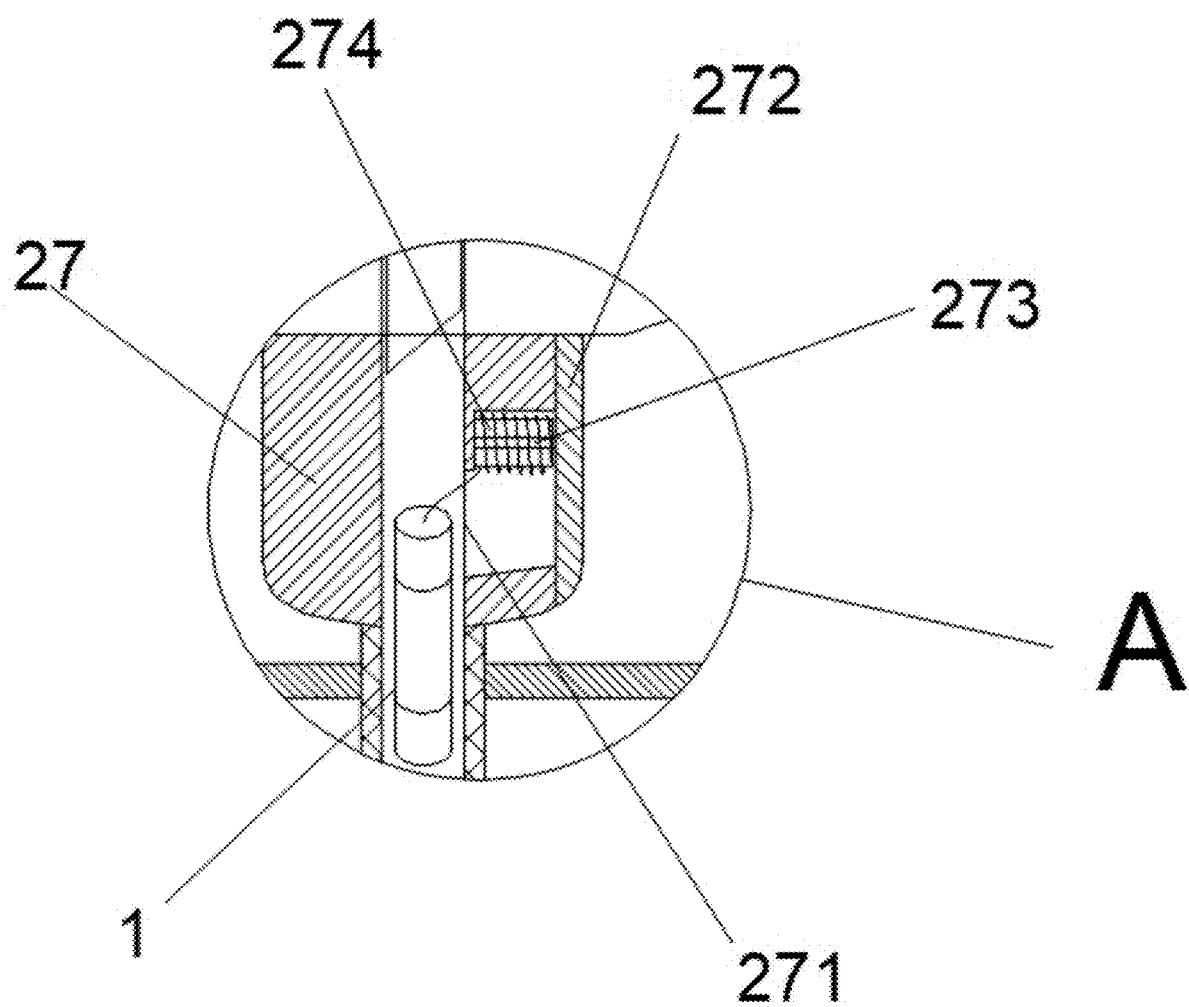
FIG. 2 is an enlarged schematic of A-zone of the embodiments of the disclosure.
Figure 3:
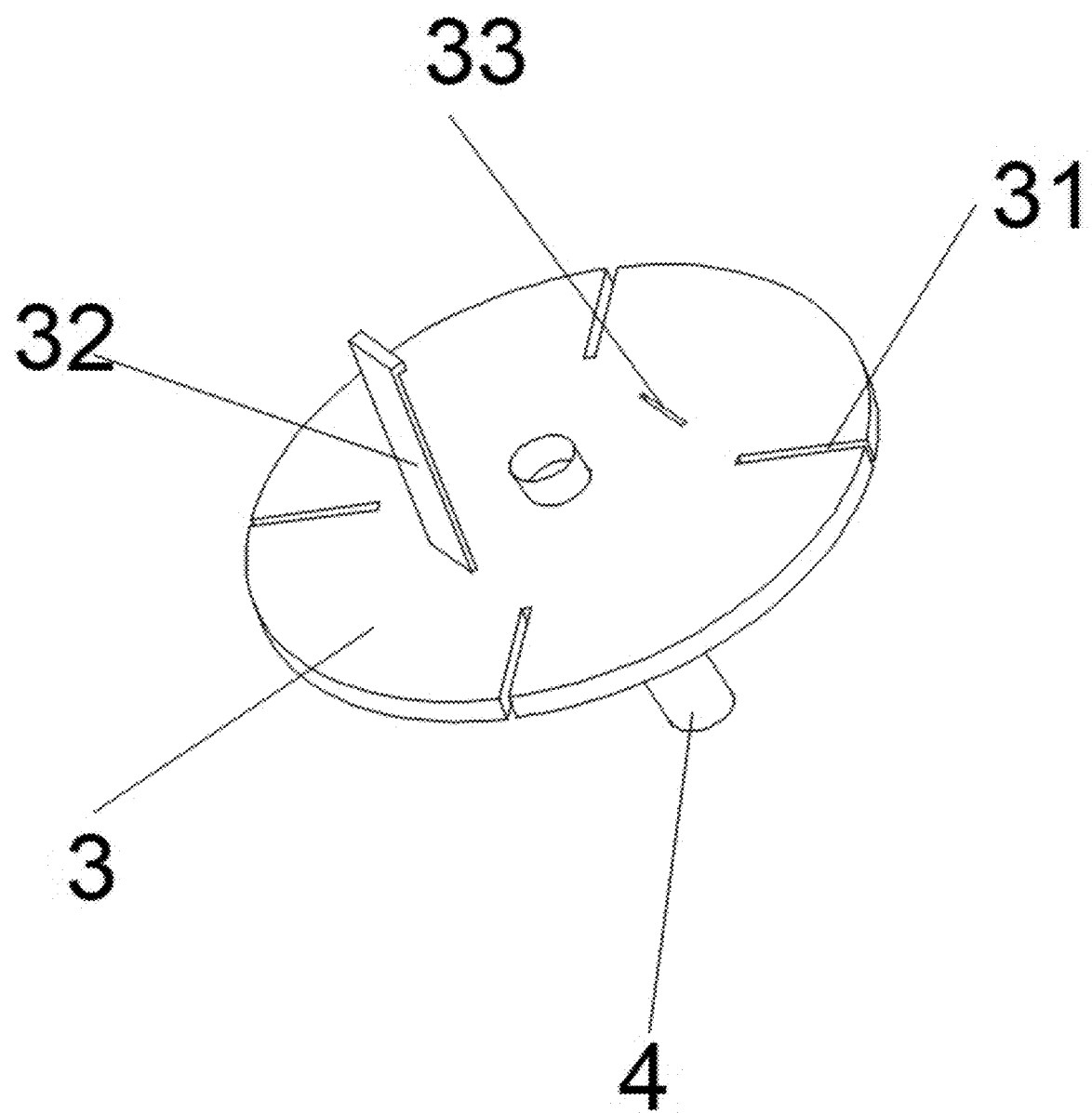
FIG. 3 is a structural schematic of the fixed disk of the embodiments of the disclosure.
Figure 4:
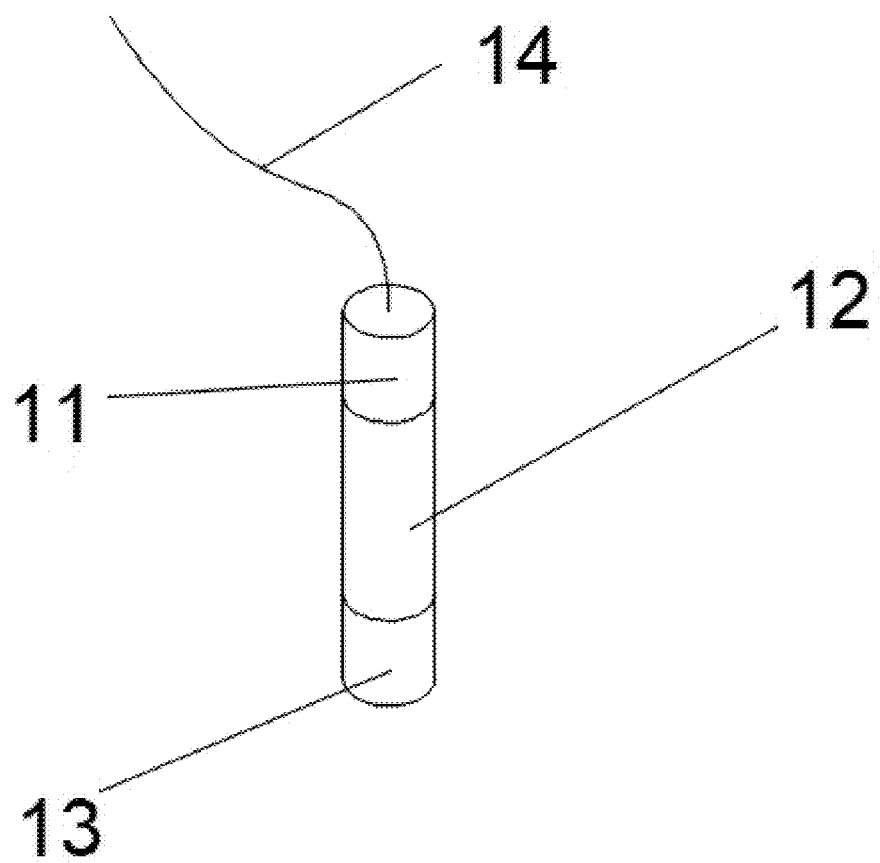
FIG. 4 is a structural schematic of the gold marker of the embodiments of the disclosure.

As shown in FIG. 1 to FIG. 4, a removable dual gold marker implantation device with minor damage includes a gold marker (1) and a puncture needle (2); the gold marker (1) is arranged in a needle barrel (21) of the puncture needle (2) when in use; the gold marker (1) comprises a gold marker head and a connecting wire (14) connected to the gold marker head, and the connecting wire (14) is a flexible medical fine line, the gold marker head comprises a first gold marker (11), a connecting part (12) and a second gold marker (13) connected in a sequential manner; the puncture needle (2) comprises a needle barrel (21) and a needle core (22); a needle tip (221) is formed at a front end of the needle core (22), and the front end of the needle core (22) is slightly smaller than the inner diameter of the needle barrel (21); a rear end of the needle barrel (21) is connected with a handle (23); an implant chamber (27) is sleeved on the rear end of the needle barrel (21); and an interior of the needle core (27) is communicated with that of the needle barrel (21). A guide sleeve (4) is sleeved on the needle barrel (21); and a rear end of the guide sleeve (4) is slidably connected with a fixed plate (3).

Further, the first gold marker (11) and the second gold marker (13) are of the same diameter and length.

Further, the length of the connecting part (12) is equal to or greater than 2 cm and less than or equal to 6 cm; the connecting part (12) is made of flexible but incompressible material. The function of the connecting part (12) is to connect the first gold marker (11) and the second gold marker (13) and to maintain a reasonable distance between the first gold marker (11) and the second gold marker (13), so as to ensure that while being implanted into the body at the same time, the two gold markers will not be compressed to each other and both of the two gold markers can play the role of positioning separately. If the first gold marker (11) and the second gold marker (13) are closely adjacent while being implanted into the body, the positioning effect of two gold markers (namely the first gold marker (11) and the second gold marker (13)) will be the same as that of just one gold marker, which can't improve the efficiency of the gold marker implantation. Further, when entering the body, without the bound of the needle barrel (21) bending deformation is possible. Due to the resistance of the tissue, the gold marker head will bend to some extent and increase the stability of the first gold marker (11) and the second gold marker (13) in the body, displacement of the gold markers in the body is thus prevented. For this purpose, the connecting part (12) could be made of high polymer material or synthetic resin, since the gold marker is made of gold with purity of 99.99%, and the connection between the gold and the high polymer material or the synthetic resin is not good, in order to realize the three-segment structure of the gold marker head, two ends of the connecting part (12) extend outwardly to wrap the gold markers, so as to effectively increase the stability of the connection; another way to increase the stability of the connection is to provide a through hole in the center of the first gold marker (11), the connecting part (12), the second gold marker (13) respectively, penetrate through the through hole of the first gold marker (11), the connecting part (12) and the second gold marker (13) with the connecting wire (14) in sequence, thus realizing the stable connection between the first gold marker (11), the connecting part (12) and the second gold marker (13) by tying up the connecting wire (14); other forms such as clasp or glue are also applicable; the connecting wire (14) is in the form of flexible medical fine line, which needs certain strength to ensure that it will not break while removing the gold marker out, and will not blend with body tissue. Common surgical suture, suture line for wound in the medical field can be used, and high molecular lines of safety and hygiene standards can also be used.

Further, a guide hole (24) communicated with the needle barrel (21) is provided in the handle (23); a position-limiting plate (25) is provided on a top end of the guide hole (24); and a push-pull part (26) is provided on a rear end of the needle core (22).

Further, the implant chamber (27) comprises an implant chamber cover (272) flexibly connected; a gold marker filling hole (271) communicated with the interior of the needle barrel (21) and a rotating shaft (273) are arranged below the implant chamber cover (272); a winding sleeve (274) is movably sleeved on the rotating shaft (273); the connecting wire (14) is enwound on the winding sleeve (274).

Further, the aperture of the gold marker filling hole (271) is larger than the diameter of the gold marker (1) and is smaller than the length of the gold marker (1).

Further, a plurality of wire clamping grooves (31) uniformly spaced apart are circumferentially distributed on the fixed plate (3);

Further, a foldable flexible folding sheet (32) and a catch groove (33) extend from the upper surface of the fixed plate (3); the folding sheet (32) is positioned directly above the guide sleeve (4) when being folded; a width of the folding sheet (32) is slightly wider than the diameter of the guide sleeve (4).

The disclosure relates to a method of use of a removable dual gold marker implant device with minor damage, which comprises the following steps:

1. Put the gold marker (1) into the needle barrel (21) through the implant chamber (27);
2. Implant the puncture needle (2) into the target area after passing through the body surface;
3. Push the needle core (22) to the bottom; the needle tip (221) pushes the gold marker (1) out of the needle barrel (21) to the target area;
4. Hold the handle (23) and remain stationary, slide the fixed plate (3) so that the fixed plate (3) is attached to the patient's skin where the puncture needle is pierced through;
5. Press the fixed plate (3) tightly and hold the guide sleeve (4) to slowly draw the needle barrel (21) out from the guide sleeve (4);
6. After the needle barrel (21) is drawn out, both the guide sleeve (4) and the connecting wire (14) in the guide sleeve (4) are clamped into one of the wire clamping grooves (31);
7. Press the folding sheet (32) so that the head of the folding sheet (32) is clamped into the catch groove (33) and the guide sleeve (4) is thus compressed by the folding sheet (32) tightly;
8. After the whole treatment, unfold the folding sheet (32); remove the guide sleeve (4) from the wire clamping groove (31) and pull the connecting wire (14) so that the gold marker head is separated from the body smoothly along the guide sleeve (4);
9. Hold the fixed plate (3) and the guide sleeve (4) simultaneously, and slowly pull the guide sleeve (4) outward to remove the guide sleeve (4) from human body.

Embodiment II

As shown in FIG. 1 to FIG. 4, a removable dual gold marker implantation device with minor damage includes a gold marker (1) and a puncture needle (2); the gold marker (1) is arranged in a needle barrel (21) of the puncture needle (2) when in use; the gold marker (1) comprises a gold marker head and a connecting wire (14) connected to the gold marker head, and the connecting wire (14) is a flexible medical fine wire, the gold marker head comprises a first gold marker (11), a connecting part (12) and a second gold marker (13) connected in a sequential manner; the puncture needle (2) comprises a needle barrel (21) and a needle core (22); a needle tip (221) is formed at a front end of the needle core (22), and the front end of the needle core (22) is slightly smaller than the inner diameter of the needle barrel (21); a rear end of the needle barrel (21) is connected with a handle (23); an implant chamber (27) is sleeved on the rear end of the needle barrel (21); and an interior of the needle core (27) is communicated with that of the needle barrel (21). A guide sleeve (4) is sleeved on the needle barrel (21); and a rear end of the guide sleeve (4) is slidably connected with a fixed plate (3).

Further, the implant chamber (27) comprises an implant chamber cover (272) flexibly connected; a gold marker filling hole (271) communicated with the interior of the needle barrel (21) and a rotating shaft (273) are arranged below the implant chamber cover (272); a winding sleeve (274) is movably sleeved on the rotating shaft (273); the connecting wire (14) is enwound on the winding sleeve (274); the aperture of the gold marker filling hole (271) is larger than the diameter of the gold marker head and smaller than the length of the gold marker head.

The gold marker can be stored in the implant chamber (27) before the implantation, which can improve the implantation efficiency and prevent the missing of the gold marker caused by bleeding when the puncture needle is inserted. The aperture of the gold marker filling hole (271) is smaller than the length of the gold marker head, which can prevent the gold marker from re-entering the implant chamber (27) when the blood is flowing back; the connecting wire (14) is enwound on the winding sleeve (274), and when the gold marker head is being pushed into the human body, the winding sleeve (274) rotates and releases the connecting wire (14) until the gold marker is fully implanted, the gold marker head then separates from the winding sleeve (274); the winding sleeve (274) is sleeved on the rotating shaft (273), and close the implant chamber cover (272) to prevent the winding sleeve (274) from being separated from the rotating shaft (273) during the rotation; the winding sleeve (274) is detachable, which facilitates the winding of the connecting wire (14) outside and also facilitates the quick replacement when it is required to re-implant the gold marker.

Embodiment III

As shown in FIG. 1 to FIG. 4, a removable dual gold marker implantation device with minor damage includes a gold marker (1) and a puncture needle (2); the gold marker (1) is arranged in a needle barrel (21) of the puncture needle (2) when in use; the gold marker (1) comprises a gold marker head and a connecting wire (14) connected to the gold marker head, and the connecting wire (14) is a flexible medical fine line, the gold marker head comprises a first gold marker (11), a connecting part (12) and a second gold marker (13) connected in a sequential manner; the puncture needle (2) comprises a needle barrel (21) and a needle core (22); a needle tip (221) is formed on a front end of the needle core (22), and the front end of the needle core (22) is slightly smaller than the inner diameter of the needle barrel (21); a read end of the needle barrel (21) is connected with a handle (23); an implant chamber (27) is sleeved on the rear end of the needle barrel (21); an interior of the implant chamber (27) is communicated with that of the needle barrel (21); a guide sleeve (4) is sleeved on the needle barrel (21), and a rear end of the guide sleeve (4) is connected with a fixed plate (3).

Further, a plurality of wire clamping grooves (31) uniformly spaced apart are circumferentially distributed on the fixed plate (3); a foldable flexible folding sheet (32) and a catch groove (33) extend from the upper surface of the fixed plate (3); the folding sheet (32) is positioned directly above the guide sleeve (4) while being folded; a width of the folding sheet (32) is slightly wider than the diameter of the guide sleeve (4).

The guide sleeve (4) is closely sleeved on the needle barrel (21), and enters the body along with the needle barrel (21) after the front portion of the needle barrel (21) is inserted into the body. A guide channel is formed in the body by the guide sleeve (4), which makes the removal of the gold marker from the body be smoother. At the same time, since the gold marker is located near the top of the guide sleeve (4), the connecting wire (14) pulls the gold marker head and is fixed in the wire clamping groove (31), Therefore, the guide sleeve (4) and the connecting wire (14) simultaneously provide a more stable traction force to the gold marker head, thus avoiding the displacement of the gold marker head.

Embodiment IV

As shown in FIG. 1 to FIG. 4, a removable dual gold marker implantation device with minor damage includes a gold marker (1) and a puncture needle (2); the gold marker (1) is arranged in a needle barrel (21) of the puncture needle (2) when in use; the gold marker (1) comprises a gold marker head and a connecting wire (14) connected to the gold marker head, and the connecting wire (14) is a flexible medical fine line, the gold marker head comprises a first gold marker (11), a connecting part (12) and a second gold marker (13) connected in a sequential manner; the puncture needle (2) comprises a needle barrel (21) and a needle core (22); a needle tip (221) is formed at a front end of the needle core (22), and the front end of the needle core (22) is slightly smaller than the inner diameter of the needle barrel (21); a rear end of the needle barrel (21) is connected with a handle (23); an implant chamber (27) is sleeved on the rear end of the needle barrel (21); and an interior of the needle core (27) is communicated with that of the needle barrel (21). A guide sleeve (4) is sleeved on the needle barrel (21); and a rear end of the guide sleeve (4) is connected with a fixed plate (3).

Further, the implant chamber (27) comprises an implant chamber cover (272) flexibly connected; a gold marker filling hole (271) communicated with the interior of the needle barrel (21) and a rotating shaft (273) are arranged below the implant chamber cover (272); a winding sleeve (274) is movably sleeved on the rotating shaft (273); the connecting wire (14) is enwound on the winding sleeve (274).

Further, a plurality of wire clamping grooves (31) uniformly spaced apart are circumferentially distributed on the fixed plate (3);

Further, a foldable flexible folding sheet (32) and a catch groove (33) extend from the upper surface of the fixed plate (3); the folding sheet (32) is positioned directly above the guide sleeve (4) while being folded; a width of the folding sheet (32) is slightly wider than the diameter of the guide sleeve (4).

The disclosure relates to a method of use of a removable dual gold marker implantation device with minor damage, which comprises the following steps:

1. Put the gold marker (1) into the needle barrel (21) through an implant chamber (27); for loading the gold marker (1), the gold marker head is first inserted into the needle barrel (21) through the gold marker filling hole (271), then the winding sleeve (274) enwound with the connecting wire (14) is sleeved on the rotating shaft (273), and then close the implant chamber cover (272) to complete the loading of the gold marker (1);

2. Implant the puncture needle (2) into the target area after passing through the body surface;

3. Push the needle core (22) to the bottom; the needle tip (221) pushes the gold marker (1) out of the needle barrel (21) to the target area; when the second gold marker is needed to be implanted, it is required to pull the puncture needle (2) out for a certain distance, so that the head portion of the puncture needle (2) could be away from the organ around the target area, and obliquely rotate the needle barrel (21) in the subcutaneous tissue for an angle greater than 15° and then insert the needle barrel (21) into the target area again, so as to form an adequate inclined angle between the second gold marker and the first gold marker; adhere the rear end of the connecting wire (14) to the implant chamber cover (272) through adhesive tape, so as to prevent the connecting wire (14) from slipping into the needle barrel (21) while loading the second gold marker; after the second gold marker is loaded, push the needle core (22) again to the bottom, and the needle tip (221) pushes the second gold marker out of the needle barrel (21) to the target area;

4. Hold the handle (23) and remain stationary, slide the fixed plate (3) so that the fixed plate (3) is attached to the patient's skin where the puncture needle is pierced through;

5. Press the fixed plate (3) tightly and hold the guide sleeve (4) to slowly draw the needle barrel (21) out from the guide sleeve (4);

6. Clamp the guide sleeve (4) and the connecting wire (14) in the guide sleeve (4) into one of the wire clamping grooves (31) after the needle barrel (21) is drawn out;

7. Press the folding sheet (32) so that a head portion of the folding sheet (32) is in clamping fit with the catch groove (33) and the guide sleeve (4) thus is being compressed tightly by the folding sheet (32);

8. After the whole treatment, unfold the folding sheet (32), remove the guide sleeve (4) from the wire clamping groove (31) and pull the connecting wire (14) so that the gold marker head is separated from the body smoothly along the guide sleeve (4);

9. Hold the fixed plate (3) and the guide sleeve (4) simultaneously and slowly pull the guide sleeve (4) outward, thus removing the guide sleeve (4) from human body.

The implantation method by the cooperation between the puncture needle and the guide sleeve provides a more convenient way for removing the gold marker. The gold marker can be removed through the guide sleeve, which can reduce the harm to the body while removing the gold marker. Further, the guide sleeve provides more stable support to the gold marker in the body, which along with the traction force of the connecting wire can effectively prevent the positioning failure caused by the displacement of the gold marker. The dual gold marker structure makes the implantation of multiple gold markers at the same time possible, which reduces the number of times of implantation and improves the efficiency.

The above description is only the preferred embodiments of the present disclosure and does not constitute a limitation to the protection scope of the present disclosure. For those skilled in this field, the present disclosure may have different variations. Any modification, substitution, improvement, etc. within the spirit and principle of the present disclosure shall fall in the scope of protection of the present disclosure.

What is claimed is:

1. A removable dual gold marker implantation device with minor damage, comprising a gold marker and a puncture needle, wherein the gold marker is arranged in a needle barrel of the puncture needle when in use; the gold marker comprises a gold marker head and a connecting wire connected to the gold marker head, and the connecting wire is a flexible medical wire, wherein the gold marker head comprises a first gold marker, a connecting part and a second gold marker connected in a sequential manner, the puncture needle comprises the needle barrel and a needle core, a needle tip is formed at a front end of the needle core, the front end of the needle core is slightly smaller than an inner diameter of the needle barrel, a rear end of the needle barrel is connected with a handle, an implant chamber is sleeved on the rear end of the needle barrel, an interior of the implant chamber is communicated with an interior of the needle barrel, a guide sleeve is sleeved on the needle barrel, and a rear end of the guide sleeve is connected with a fixed plate, wherein the first gold marker, the connecting part, and the second gold marker are of the same diameter and wherein the connecting part is made of a flexible but incompressible material.

2. A removable dual gold marker implantation device with minor damage according to claim 1, wherein the first gold marker and the second gold marker are of the same length.

3. A removable dual gold marker implantation device with minor damage according to claim 1, wherein a length of the connecting part is equal to or greater than 2 cm and less than or equal to 6 cm.

4. A removable dual gold marker implantation device with minor damage according to claim 1, wherein a guide hole communicated with the needle barrel is provided in the handle, a position-limiting plate is provided on a top of the guide hole, and a push-pull part is provided on a rear end of the needle core.

5. A removable dual gold marker implantation device with minor damage according to claim 1, wherein the implant chamber comprises an implant chamber cover flexibly connected, a gold marker filling hole communicated with the interior of the needle barrel and a rotating shaft are arranged under the implant chamber cover, and a winding sleeve is movably sleeved on the rotating shaft, the connecting wire is enwound on the winding sleeve.

6. A removable dual gold marker implantation device with minor damage according to claim 5, wherein an aperture of the gold marker filling hole is greater than a diameter of the gold marker head and smaller than a length of the gold marker head.

7. A removable dual gold marker implantation device with minor damage according to claim 1, wherein a plurality of wire clamping grooves uniformly spaced apart are circumferentially distributed on the fixed plate.

8. A removable dual gold marker implantation device with minor damage according to claim 1, wherein a foldable flexible folding sheet and a catch groove extend from an upper surface of the fixed plate, the foldable flexible folding sheet is positioned directly above the guide sleeve when being folded, and a width of the foldable flexible folding sheet is slightly wider than a diameter of the guide sleeve.

* * * * *